US007467870B2

(12) United States Patent
van de Kraats et al.

(10) Patent No.: US 7,467,870 B2
(45) Date of Patent: Dec. 23, 2008

(54) REFLECTOMETRY INSTRUMENT AND METHOD FOR MEASURING MACULAR PIGMENT

(75) Inventors: Jan van de Kraats, Putten (NL); Dirk van Norren, Leusden (NL); Tos T. J. M. Berendschot, Maastricht (NL)

(73) Assignee: ZeaVision LLC, St. Louis, MO (US)

( * ) Notice: Subject to any disclaimer, the term of this patent is extended or adjusted under 35 U.S.C. 154(b) by 237 days.

(21) Appl. No.: 11/412,993

(22) Filed: Apr. 27, 2006

(65) Prior Publication Data

US 2007/0252950 A1 Nov. 1, 2007

(51) Int. Cl.
*A61B 3/10* (2006.01)
(52) U.S. Cl. .................... 351/221; 351/206; 351/214
(58) Field of Classification Search ............ 351/200, 351/205, 206, 207, 213, 214, 220, 221, 246
See application file for complete search history.

(56) References Cited

U.S. PATENT DOCUMENTS

| | | | |
|---|---|---|---|
| 4,861,154 A | 8/1989 | Sherwin et al. | |
| 4,889,422 A | 12/1989 | Pavlidis | |
| 5,331,969 A | 7/1994 | Silberstein | |
| 6,315,412 B1 | 11/2001 | Snodderly | |
| RE38,009 E | 2/2003 | Garnett et al. | |
| 6,572,229 B2 | 6/2003 | Wei | |
| 6,578,965 B2 | 6/2003 | Grant | |
| 6,623,117 B2 | 9/2003 | Shibutani et al. | |
| 6,688,744 B2 | 2/2004 | Wei et al. | |
| 6,729,728 B2 | 5/2004 | Wei et al. | |
| 6,834,958 B2 | 12/2004 | Cornsweet et al. | |
| 6,969,856 B1 | 11/2005 | Hillenbrand et al. | |
| 7,156,518 B2* | 1/2007 | Cornsweet et al. | 351/246 |
| 2003/0130579 A1* | 7/2003 | McClane et al. | 600/476 |

OTHER PUBLICATIONS

"Fast and Objective Measurement Of Macular Pigment With Natural Pupil" (Dirk van Norren, Jan van de Kraats, Suze Valen & Tos T.J.M. Berendschot) Apr. 30, 2005—(1-page).
"Fundus Photography For Measurement Of Macular Pigment Density Distribution in Children" (Lo J. Bour, Lily Koo, Francois C. Delort, Patricia Apkarian, Anne B. Fulton) Investigative Ophthalmology & Visual Science, May 2002, vol. 43, No. 5 Copyright © Association for Research in Vision and Ophthalmology—(7-pages).

(Continued)

*Primary Examiner*—Huy K Mai
(74) *Attorney, Agent, or Firm*—Nixon Peabody LLP

(57) ABSTRACT

A reflectometry instrument includes a light source, a spectrometer, and a first and second lens. The light source emits an illumination beam to the macula. The spectrometer measures a detection beam that is a portion of the illumination beam reflected from the eye and is indicative of the eye characteristics (e.g. macular pigment). The first and second lenses transmit the illumination beam to the macula and transmit the detection beam from the macula to the spectrometer. The instrument is used on an undilated pupil and minimizes unwanted reflections by at least one of the following: the first and second lenses include anti-reflection coatings; the illumination and detection beams pass through the first and second lenses at locations offset from their centers; and the illumination and the detection beams remain separated when passing through the first and second lenses. Zeaxanthin, lutein, and the total macular pigment levels are measured by the instrument.

36 Claims, 9 Drawing Sheets

OTHER PUBLICATIONS

"Comparison Of Fundus Autofluorescence and Minimum-Motion Measurements Of Macular Pigment Distribution Profiles Derived From Identical Retinal Areas" Anthony G. Robson, Glen Harding, Frederick W. Fitzke, Jack D. Moreland "Perception" vol. 34 2005—www.perceptionweb.com—(7-pages).

"Macular Pigment Assessment By Motion Photometry" Moreland JD.—MacKay Institute, Keele University, Staffordshire, ST5 5BG, UK. j.d.moreland@cns.keele.ac.uk PubMed—Arch Biochem Biophys. Oct. 15, 2004; 430(2):143-8—(1-page).

"Macular Pigment Optical Density Measurement: A Novel Compact Instrument" Stephen Beatty, Hui-Hiang Koh, David Carden and Ian J. Murray, Ophthal. Physical Opt. vol. 20, No. 2, pp. 105-111, 2000 © 2000 The College of Optometrists, Published by Elsevier Science Ltd. Printed in Great Britain—(7-pages).

"A Practical Method For Measuring Macular Pigment Optical Density" Billy R. Wooten, Billy R. Hammond, Jr., Richard I. Land and D. Max Snodderly Investigation Ophthalmology and Visual Science. 1999;40:2481-2489. © 1999 by The Association For Research In Vision and Ophthalmology, Inc. (14 pages).

"Macular Pigment Measurement By Heterochromatic Flicker Photometry In Order Subjects: The Carotenoids And Age-Related Eye Disease Study" D. Max Snodderly, Julie A. Mares, Billy R. Wooten, Lisa Oxton, Michael Gruber, and Tara Ficek, for the AREDS Macular Pigment Study Group Investigative Ophthalmology & Visual Science, Feb. 2004, vol. 45, No. 2 Copyright © Association for Research in Vision and Ophthalmology.—(8-pages).

"Macular Pigment" Property of the University of Westminster, Vision Research Group John Mellerio—melleri@wmin.ac.uk—(10 pages).

"Heterochromatic Flicker Photometry" Department of Physics, Florida International University, Miami 33199, USA Bone RA, Landrum JT.—bone@fiu.edu PubMed—Arch Biochem Biophys. Oct. 15, 2004;430(2):137-42—(1page).

"A Portable Instrument For Measuring Macular Pigment With Central Fixation" Mellerio J, Ahmadi-Lari S, van Kuijk F, Pauleikhoff D, Bird A, Marshall J. (1 page).

"Macular Pigment Density Measured By Autofluorescence Spectrometry: Comparison with Reflectometry and Heterochromatic Flicker Photometry" Delori FC, Goger DG, Hammond BR, Snodderly DM, Burns SA. Schepens Eye Research Institute, Boston, Massachusetts 02114, USA. PubMed—Opt Soc Am A Opt Image Sci Vis. Jun. 2001;18(6):1212-30.—(1 page).

"Autofluorescence Method To Measure Macular Pigment Optical Densities Fluorometry And Autofluorescence Imaging" Francois C. Delori Schepens Eye Research Institute and Harvard Medical School, Boston, M.A. USA © 2004 Published by Elsevier Inc.—(7 pages).

"Resonance Raman Measurement of Macular Carotenoids In The Living Human Eye" Paul S. Bernstein, Da-You Zhao, Mohsen Sharifzadeh, Igor V. Ermakov , Werner Gellermann Department of Ophthalmology and Visual Sciences, Moran Eye Center, University of Utah School of Medicine, Salt Lake City, UT, USA, Department of Physics, University of Utah, Salt Lake City, UT © 2004 Elsevier Inc.—(7 pages).

"Influence of Lutein Supplementation On Macular Pigment, Assessed with Two Objective Techniques" T. J. M. Berendschot[1], R. Alexandra Goldbohm [2], Wilhelmina A.A. Klöpping [2], Jan van de Kraats[1], Jeannette van Norel [1], and Dirk van Norren [1] © 2000 by The Association for Research in Vision and Ophthalmology, Inc.—(1 page).

"Influence Of Lutein Supplementation On Macular Pigment, Assessed With Two Objective Techniques" Berendschot TT, Goldbohm RA, Klopping WA, van de Kraats J, van Norel J, van Norren D. University Medial Centre Utrecht, Department of Ophthalmology, The Netherlands PubMed—Invest Ophthal. Vis. Sci. Oct. 2000; 41(11):3322-6.—(1 page).

"Objective Determination Of The Macular Pigment Optical Density Using Fundus Reflectance Spectroscopy" Tos T.J.M. Berendschot * and Dirk van Norren Department of Ophthalmology, University Medical Center Utrecht, The Netherlands © 2004 Elsevier, Inc.—(7-pages).

"Current Concepts In The Pathogenesis Of Age-Related Macular Degeneration" Marco A. Zarbin, MD, PhD. Arch Ophthalmol./vol. 122. Apr. 2004—www.archophthalmol.com © 2004 American Medical Association.—(17 pages).

"Assessment Of The Validity Of In Vivo Methods Of Measuring Human Macular Pigment Optical Density" Hammond BR Jr., Wooten BR, Smollon B. Vision Science Laboratory, University Of Georgia, Athens, Georgia 30602-3013, USA PubMed—Optom Vis. Sci. May 2005; 82(5):387-404—(1 page).

In Vivo Assessment Of Retinal Carotenoids: Macular Pigment Detection Techniques and Their Impact On Monitoring Pigment Status Joanne Curran Celentano, Joanne D. Burke and Billy R Hammond, Jr.Department of Animal and Nutritional Sciences, University of New Hampshire, Durham, NH and Department of Psychology and Behavior Sciences, University of Georgia, Athens, GA © 2000 American Society For Nutritional Sciences—(5 pages).

"Macular Degeneration—The Latest Scientific Discoveries and Treatments For Preserving Your Sight" Robert D'Amato, M.D., Ph.D., and John Snyder Copyright © by Robert d' Amato and Joan Snyder—(2 pages).

"Age-Related Macular Degeneration" Jeffrey W. Gerger, Stuart L. Fine and Maureen G. Maguire, Mosby, 1999.Jul. 2002 / 576 pp, illus. /ISBN: 08247-0682-X—(3-pages).

J. van. de. Kraats, T.T.J.M. Berendschot, and D. van Norren, "The pathways of light measured in fundus reflectometry," Vision Res. 36, 2229-2247 (1996).

F.C. Delori and K.P. Pfibsen, "Spectral reflectance of the human ocular fundus," Appl. Opt. 28, 1061-1077 (1989).

V.P. Gabel, R. Birngruber, and F. Hillenkamp, "Visible and near infrared light absorption in pigment epithelium and choriod," in *Excerpta Medica, International Congress Series* No. 450, K. Shimizu and J.A. Oosterhuis, eds, (Elsevier, Amsterdam, 1978), pp. 658-662.

G.J. Handelman, D.M. Snodderly, N.I. Krinsky, M.D. Russett, and A.J. Alder, "Biological control of primate macular pigment. Biochemical and densitometric studies," Invest. Ophthalmol. Vis. Sci. 32, 257-267 (1991).

J. Pokorny, V.C. Smith, and M. Lutze, "Aging of the human lens," Appl., Opt. 26, 1437-1440 (1987).

O.W. van Assendelft, *Spectroscopy of hemoglobin derivatives,* C.C. Thomas ed., (C.C. Thomas, Springfield, IL, 1979) (pp. 54-57).

D. van Norren and L. F. Tiemeijer, "Spectral reflectance of the human eye," Vision Res. 26, 313-320 (1986).

"Fundus Photography for Measurement of Macular Pigment Density Distribution in Children" Lo J. Bour, Lily Koo, Francois C. Delori, Patricia Apkarian, and Anne B. Fulton—Investigative Ophthalmology & Visual Science, May 2002, vol. 43, No. 5—6 pages.

"Macular Pigment Assessment by Motion Photometry" J.D. Moreland—MacKay Institute, Keele University, Staffordshire, UK—Archives of Biochemistry and Biophysics 430 (2004) 143-148—6 pages.

"Heterochromatic Flicker Photometry" Richard A. Bone and John T. Landrum—Department of Physics, Department of Chemistry & Biochemistry, Florida International University, Miami, Florida—Archives of Biochemistry and Biophysics 430 (2004) 137-142—6 pages.

"A Portable Instrument for Measuring Macular Pigment with Central Fixation" J. Mellerio, S. Ahmadi-Lari, F.J.G.M. van Kuijk, D. Pauleikhoff, A.C. Bird and J. Marshall—Current Eye Research—2002, vol. 25, No. 1, 37-47—11 pages.

"Macular Pigment Density Measured by Autofluorescence Spectrometry: Comparison with Reflectometry and Heterochromatic Flicker Photometry" Francois C. Delori, Douglas G. Goger, Billy R. Hammond, D. Max Snodderly and Stephen A. Burns—Schepens Eye Research Institute, Boston, MA and Harvard Medical School, Boston, MA—J. Opt. Soc. Am. A, vol. 18, No. 6, Jun. 2001—1212-1230—19 pages.

"Influence of Lutein Supplementation on Macular Pigment, Assessed with Two Objective Techniques" Tos. T. J. M. Berendschot, R. Alexandra Goldbohm, Wilhelmina A. A. Klöpping, Jan van de Kraats, Jeannette van Norel and Dirk van Norren—Investigative Ophthalmology & Visual Science, Oct. 2000, vol. 41, No. 11—5 pages.

"Assessment of the Validity of *in Vivo* Methods of Measuring Human Macular Pigment Optical Density" Billy R. Hammond, Jr., Billy R. Wooten and Bill Smollon—University of Georgia, Athens, GA and Brown University, Providence, RI—Optometry and Vision Science, vol. 82, No. 5, May 2005—17 pages.

* cited by examiner

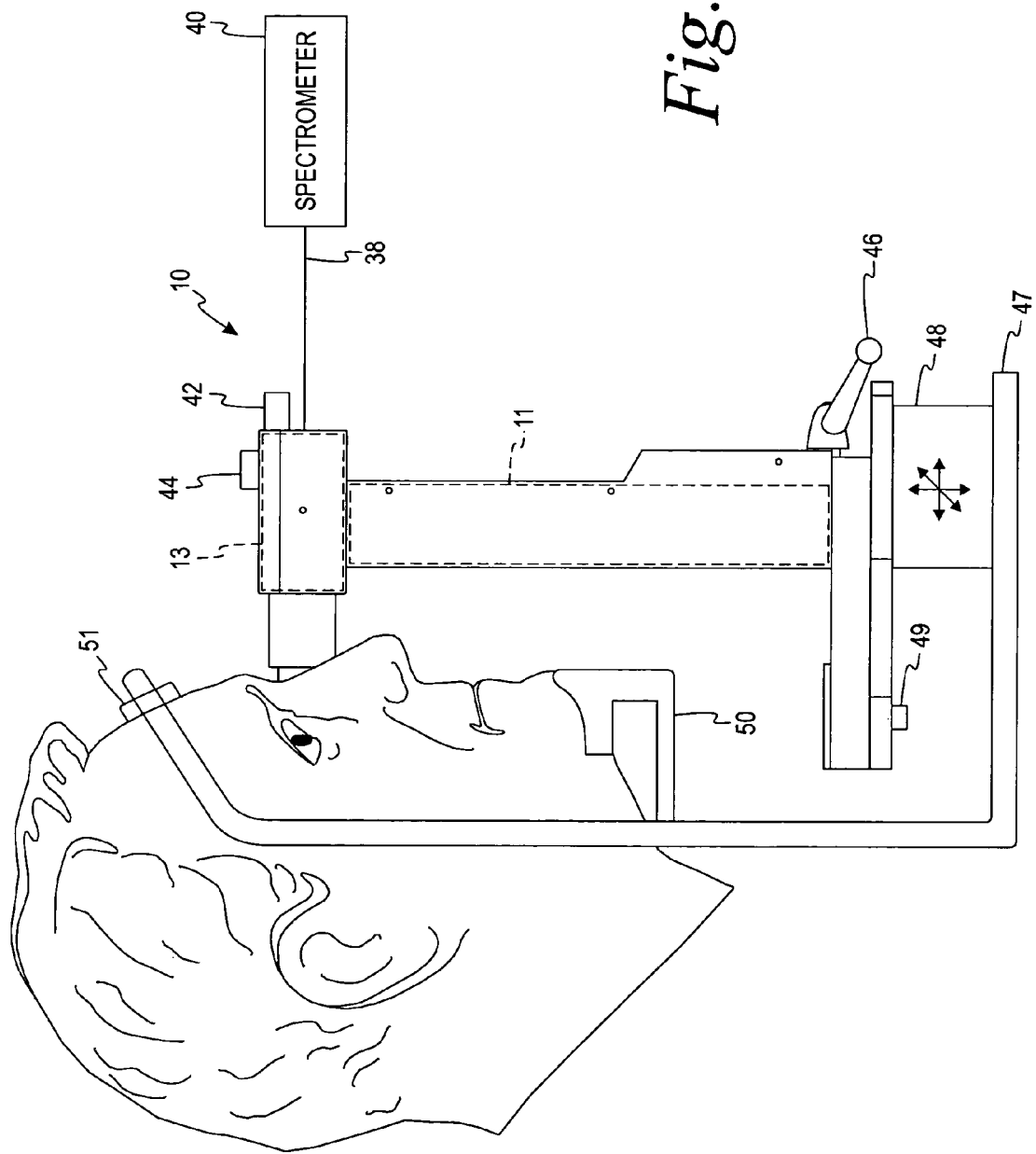

REFLECTOMETRY INSTRUMENT AND METHOD FOR MEASURING MACULAR PIGMENT

FIELD OF THE INVENTION

The present invention relates to a reflectometry instrument that measures characteristics of the patient's eye, such as macular pigment, with a high degree of accuracy and without dilating the patient's pupil.

BACKGROUND OF THE INVENTION

The retina is the layer of nerve cells at the back of the eye, which convert light into nerve signals that are sent to the brain. In humans, and in other primates (but not in most other mammals, or other types of animals), the retina has a small yellowish area in the center of the field of vision. That yellowish area is called the "macula." It provides fine-resolution vision in the center of the visual field and is essential to good vision. People who suffer from macular degeneration often lose the ability to read, recognize faces, drive, or walk safely on unfamiliar routes.

The surrounding portions of the macula can only provide coarse resolution. This physiological feature limits and controls the number of nerve signals that the brain must rapidly process, to form coherent rapid-response vision, and it also helps limit and control the huge number of rod and cone receptors that the eye must continually regenerate and recycle, every day. Many people do not realize the retina can provide only coarse resolution, outside of a limited central area, because the eyes and the brain have developed an extraordinary ability to synthesize coherent vision from a combination of fine and coarse resolution. During that type of vision synthesis, the eye muscles cause the eyes to flit back and forth over a larger field of vision, pausing at each location for just an instant while the eye quickly "grabs" a fine-resolution image of a limited area. This process occurs so rapidly that a person does not notice it happening, and does not pay attention to how a complete visual image and impression is being assembled and updated from combinations of fine and coarse resolution images.

There is also a peculiar anatomic structure in the retinas of humans, which points out the difference between fine resolution (provided by the macula) and coarse resolution (provided by the remainder of the retina). In humans, the blood vessels that serve the retina actually sit in front of the retina, where they can block and interfere with incoming light, before the light reaches the retina. This is counter-intuitive, and one should wonder why the retina evolved with a physical handicap that literally gets in the way of good, clear vision. The answer is, in those parts of the retina, only coarse vision is being created, and blood vessels positioned in front of the retina do not interfere with that type of coarse vision. By contrast, in the macular region in the center of the retina, the blood vessels in front of the retina are lacking and supply is only from blood vessels present anywhere behind the layer of neurons with rod and cone receptors. This is consistent with the macula providing fine resolution vision, which would be blocked and hindered if the blood vessels were located in front of the neurons, in ways that would intercept and blocking portions of the incoming light.

"Retinal degeneration" is a descriptive term, which refers to and includes an entire class of eye diseases and disorders. It includes any progressive disorder or disease that causes the macula to gradually degenerate, to a point that substantially impairs or damages eyesight and vision. Several major categories of retinal degeneration are known. These include: (i) age-related macular degeneration, which gradually appears among some people over the age of about 65; (ii) diabetic retinopathy, in which problems with sugar and energy metabolism damage the entire retina, including the macula; (iii) eye diseases that affect the macula due to gene and/or enzyme defects, such as Stargardt's disease, Best's disease, Batten's disease, Sjogren-Larsson syndrome, and various other eye disorders that lead to gradual degeneration of the macula (and possibly other parts of the retina) over a span of time. This is not an exclusive list, and other subclasses and categories also are known. For example, age-related macular degeneration is subdivided into wet and dry forms, depending on whether abnormal and disruptive blood vessel growth is occurring in the structural layers behind the retina.

The causes and effects of macular degeneration, and efforts to prevent or treat it, are described in numerous books (e.g., "Macular Degeneration," by Robert D'Amato et al (2000) and "Age-Related Macular Degeneration," by Jennifer Lim (2002)), articles ("Age-Related Macular Degeneration" by Berger et al (1999)) and patents, such as U.S. Pat. No. Re. 38,009, which is assigned to ZeaVision LLC, and is incorporated by reference in its entirety.

In recent years, awareness has grown, among some researchers but not among the general public, of the roles that macular pigment plays, in the health and longevity of the macula. Therefore, the two carotenoid pigments that create and provide the macular pigment are discussed below.

The Macular Pigments: Zeaxanthin and Lutein: The macula has a yellowish color because it contains unusually high concentrations of two specific pigments, called zeaxanthin and lutein. Both are carotenoids, similar to beta-carotene but with hydroxy groups coupled to their end rings (the presence of one or more oxygen atoms causes a carotenoid to be categorized as a "xanthophyll", so zeaxanthin and lutein are sometimes referred to as xanthophylls). Both of those two carotenoids are known to be protective and beneficial, in human retinas, by mechanisms that include: (1) absorption of destructive ultraviolet photons; and (2) quenching of destructive radicals. Both of those mechanisms, and other potential protective mechanisms, are discussed below.

In addition to their involvement in the macula and macular degeneration, zeaxanthin and lutein also are present in other eye structures (including the eye lens), and undesirably low levels of those two carotenoids appear to be correlated with higher risks of disorders such as cataracts. Accordingly, although the discussion herein focuses on macular degeneration, it should be recognized that any comments herein about macular pigment levels also have varying degrees of relevance to some other eye disorders as well. Similarly, any comments herein about macular degeneration should be recognized as including disorders that are referred to by other names (such as diabetic retinopathy, Stargardt's disease, etc.), but that involve or lead to gradual deterioration of the macula.

The structures of zeaxanthin and lutein are very similar because they are isomers of each other, differing only in the placement of a double bond in one end ring. In lutein, the ring with a "misplaced" double bond is called an "epsilon" ring. All of the other end rings have "beta" ring structures, which refer to the sequence of double bonds found in beta-carotene's two end rings.

However, that single minor structural difference, between zeaxanthin versus lutein, has profound effects on the traits, performance, and tissue concentrations of those two different molecules, in both plants and animals. Briefly, the lutein molecule has a bend where the epsilon ring joins the "straight chain" segment between the two end rings. That bend, near one end, allows lutein to fit properly into ring-shaped "light-harvesting" structures, in the chloroplasts of plant cells. Since light-harvesting (which is part of photosynthesis) is crucial in plants, lutein evolved as a major and dominant carotenoid, in essentially all plants.

By contrast, zeaxanthin does not have a bend at either end. Since it is relatively straight, it cannot fit properly into the circular light-harvesting structures that help carry out photosynthesis, in plants. Therefore, it evolved in plants in ways that led to a very different role in a day-night cycle, in which zeaxanthin and a similar carotenoid called violaxanthin are converted back and forth into each other. As a result, zeaxanthin does not accumulate in substantial quantities in most types of plants (although a few exceptions are known, such as corn and red peppers). Even in dark green plants, such as spinach or kale, lutein content is dozens or even hundreds of times greater than zeaxanthin content. On an aggregate basis, the total amount of zeaxanthin in typical diets in industrial nations is believed to be about 1% (or possibly even less) of the total lutein supply.

Another important difference between zeaxanthin and lutein is that zeaxanthin has a longer and more protective "conjugated cloud" of electrons surrounding it, compared to lutein. When a series of carbon atoms are bonded to each other by alternating double and single bonds, the electrons become mobile, and are no longer affixed to specific bond locations. Those electrons form a flexible and movable electron "cloud". This same type of cloud also appears in benzene rings and other "aromatic" organic compounds, and it is well-known to chemists.

That type of flexible and movable electron cloud is ideally suited for absorbing high-energy radiation (in the ultraviolet, near-ultraviolet, and deep blue part of the spectrum), without suffering damage or breakage of the molecule. In addition, a flexible and movable electron cloud is ideally suited for neutralizing and "quenching" oxygen radicals, which are aggressively unstable and destructive molecules, containing oxygen atoms having unpaired electrons. Oxidative radicals are important damaging agents in any cells and tissues that are being bombarded by high levels of UV radiation, since UV radiation often breaks bonds that involve oxygen atoms, in ways that create unpaired electrons where the broken bonds previously existed.

All carotenoids are assembled, in plants, from a 5-carbon precursor called isoprene, which has two double bonds separated by a single bond. As a result, all carotenoids have at least some sequence of alternating double and single bonds, leading to a conjugated electron cloud covering at least part of the carotenoid molecule. This is a basic and shared trait of all carotenoids, and it explains how carotenoids provide two crucial benefits (i.e., absorption of UV radiation, and quenching of destructive radicals) that are vital to plants, which must often sit in direct sunlight for hours each day.

However, different carotenoids have conjugated electron clouds that different lengths, and different potencies and protective traits. In particular, there is a crucial difference between the conjugated electron clouds of zeaxanthin and lutein. The placement of the double bonds in both of zeaxanthin's two end rings continues and extends the pattern of alternating double and single bonds, from the straight chain. This extends zeaxanthin's conjugated and protective electron cloud, out over a part of both of zeaxanthin's two end rings.

By contrast, the position of the double bond in lutein's "epsilon" ring disrupts the alternating double/single bond sequence, established by the straight-chain portion of the molecule. This disrupts and terminates the conjugated electron cloud, and it prevents the protective, UV-absorbing, radical-quenching electron cloud from covering any part of lutein's epsilon end ring. That structural-difference in their end rings becomes highly important, because zeaxanthin and lutein are deposited into animal cells in ways that cause them to "span" or "straddle" the outer membranes of the cells. It causes zeaxanthin and lutein to be deposited into animal cell membranes in a way that places them perpendicular to the surfaces of the membrane that surrounds and encloses a cell.

It is not fully known, at a molecular level, how lutein's lack of symmetry, and lack of a protective conjugated electron cloud over one end ring, affect its deposition in cells in the human macula. For example, it is not known whether the protective beta rings at one end of lutein are consistently or predominantly placed on either the external or internal surfaces of cell membranes. In addition, it is not known whether lutein is consistently deposited, into human cell membranes, in a membrane-spanning orientation.

However, other aspects of zeaxanthin and lutein content and deposition in blood, and in the macular regions of human retinas, are well-known. Despite the rarity of zeaxanthin in food sources (as mentioned above, zeaxanthin content in typical diets is believed to be less than about 1% of the lutein supply), zeaxanthin concentrations in human blood average about 20% of lutein levels. This clearly indicates that the human body does something that indicates a selective preference for zeaxanthin, over lutein.

Even more revealingly, zeaxanthin is even more concentrated in the crucially important center of the human macula, which provides fine-resolution vision in humans. In the crucially important center of a healthy human macula, zeaxanthin is present at levels that average more than twice the concentrations of lutein. By contrast, lutein is present in higher levels around the less-important periphery of the macula. While the mechanisms which create that pattern of deposition are not fully understood, it recently has been reported that certain enzymes that appear to be involved will clearly bind to zeaxanthin with relatively high affinity under in vitro conditions; however, those same enzymes will not bind to lutein with any substantial affinity (Bhosale et al 2004).

Accordingly, these differences in how zeaxanthin and lutein are deposited in the macula provide strong evidence that the macula wants and needs zeaxanthin, more than lutein. The patterns of deposition, and the known structural and electron cloud differences, suggest and indicate that the macula wants and needs zeaxanthin, and it uses lutein only if and when it cannot get enough zeaxanthin.

This belief is also supported by another important finding. The macula may attempt to convert lutein into zeaxanthin. However, the conversion process cannot convert lutein into the normal stereoisomer of zeaxanthin found in plants and in the diet (the 3R,3'R stereoisomer). Instead, it converts lutein into a different stereoisomer that has never been found in any food sources or mammalian blood. That non-dietary isomer has one end ring with the conventional "R" configuration; however, the second end ring has an unnatural "S" configuration that is never found in the normal diet. That S-R isomer (and R-S isomer) is called meso-zeaxanthin.

Consequently, while lutein may have benefits, a growing body of knowledge and evidence indicates that zeaxanthin is the ideal carotenoid for helping prevent and treat the class of eye diseases that fall into the category of retinal degeneration.

To address problems associated with retinal degeneration in a patient, instruments are needed to help measure the macular pigment within the patient's eye. While various instruments exist that can perform this function, improvements are needed to provide instruments that are more accurate, easier to use, and less time consuming. For example, many instruments require the eye to be dilated before use, which can be uncomfortable to the patient and add extra time and cost to the procedure.

The present invention is directed to an improved reflectometer instrument that can measure the macular pigment within the eye of the patient without the need to dilate the eye. The improved reflectometer also provides the ability to measure the various constituents of the macular pigment, including lutein and zeaxanthin.

SUMMARY OF THE INVENTION

According to one aspect of the present invention, a reflectometry instrument is provided to measure the macular pigment of a macula of a human eye. The reflectometry instrument includes a light source, a spectrometer, a first lens, and a second lens. The light source emits an illumination beam in the direction toward the macula. The spectrometer measures a detection beam where the detection beam is a portion of the illumination beam reflected from the macula and is indicative of the amount of macular pigment in the macula. The first lens, which includes an anti-reflection coating, is adapted to transmit the illumination beam to the macula and also transmits the detection beam from the macula to the spectrometer. A second lens is adapted to transmit the illumination beam to the macula and also is adapted to transmit the detection beam from the macula to the spectrometer. The second lens is disposed adjacent to the first lens and includes an anti-reflection coating. The illumination beam and the detection beam remain separated when the illumination beam and the detection beam pass through the first lens and the second lens. The anti-reflection coating and beam separation helps to minimize the leaking of backscattered light from the illumination beam into the detection beam.

According to another aspect of the present invention, a reflectometry instrument is provided to measure the macular pigment of a macula of a human eye. The reflectometry instrument includes a light source, a spectrometer, a first lens, and a second lens. The light source is adapted to emit an illumination beam in a direction toward the macula. The spectrometer measures a detection beam where the detection beam is a portion of the illumination beam reflected from the macula and is indicative of the amount of macular pigment in the macula. The first lens is adapted to transmit the illumination beam to the macula at a location offset from the center of the first lens. The first lens is also adapted to transmit the detection beam from the macula to the spectrometer at another location offset from the center of the lens. The second lens, disposed adjacent to the first lens, is adapted to transmit the illumination beam to the macula at a location offset from the center of the second lens. The second lens is further adapted to transmit the detection beam from the macula to the spectrometer at another location offset from the center of the second lens. The illumination beam and the detection beam are spatially separated when the illumination beam and the detection beam pass through the first lens and the second lens. The offset from the central axes of the lenses and the beam separation helps to minimize the leaking of backscattered light from the illumination beam into the detection beam.

According to yet another aspect of the present invention, a method of determining the amount of macular pigment in the macula of a human eye is disclosed. The method includes the act of passing an illumination beam through a lens system having a first lens and a second lens. The illumination beam passes through the first lens and the second lens offset from the centers of the first lens and second lens. In response to passing through the lens system, the method further includes directing the illumination beam onto the macula so as to produce a detection beam exiting from the eye. The method additionally includes the act of passing the detection beam through the lens system offset from the centers of the first lens and second lens. The detection beam and the illumination beam avoid the central regions at the first lens and the second lens. The specular reflections of the illumination beam are minimized in the detection beam. The method further includes receiving the detection beam at a spectrometer and measuring the characteristics of the detection beam. The characteristics may include the total macular pigment amount, the macular pigment amounts of zeaxanthin and lutein, and/or the amounts of pigment in the patient's lens.

Additional aspects of the invention will be apparent to those of ordinary skill in the art in view of the detailed description of various embodiments, which is made with reference to the drawings, a brief description of which is provided below.

BRIEF DESCRIPTION OF THE DRAWINGS

FIG. 3 illustrates a side view of the reflectometry instrument as used on a human eye.

DETAILED DESCRIPTION

Figure 1:
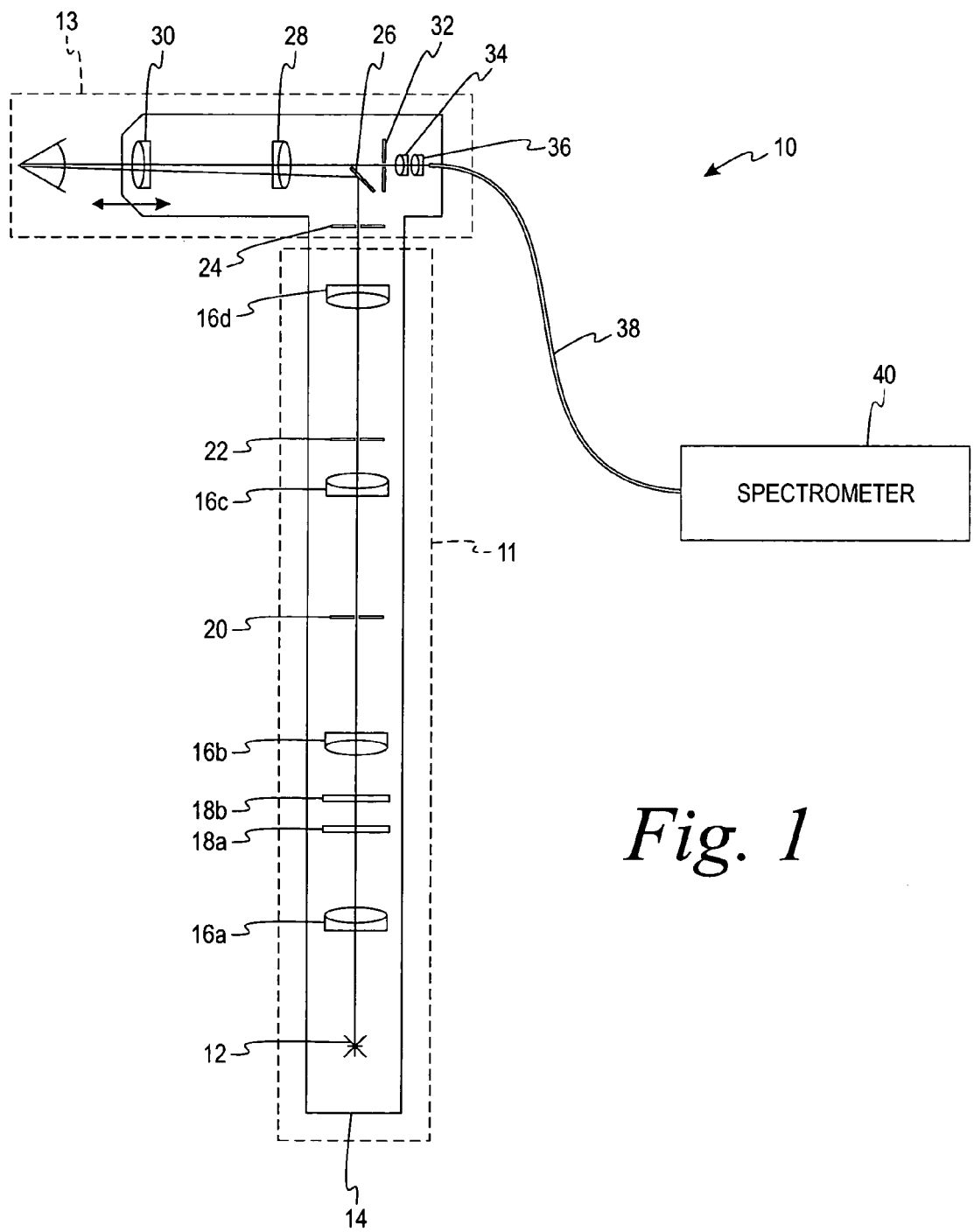
FIG. 1 is an optical schematic of a reflectometry instrument according to the present invention.

FIG. 1 illustrates a reflectometry instrument 10 adapted to measure the characteristics of a human eye. The reflectometry instrument 10 will be described in reference to two main portions—a source system 11 and a beam separation system 13. The source system 11 includes a light source 12, a plurality of source lenses 16, filters 18, a filament mask 20, and a retinal stop 22. The source system 11 generates an illumination beam having certain characteristics that will be transmitted to the patient's eye. As mentioned above, the reflectometry instrument 10 may be used on an undilated pupil, making the system much easier to use and decreasing the time required to test a patient.

Figure 2A:
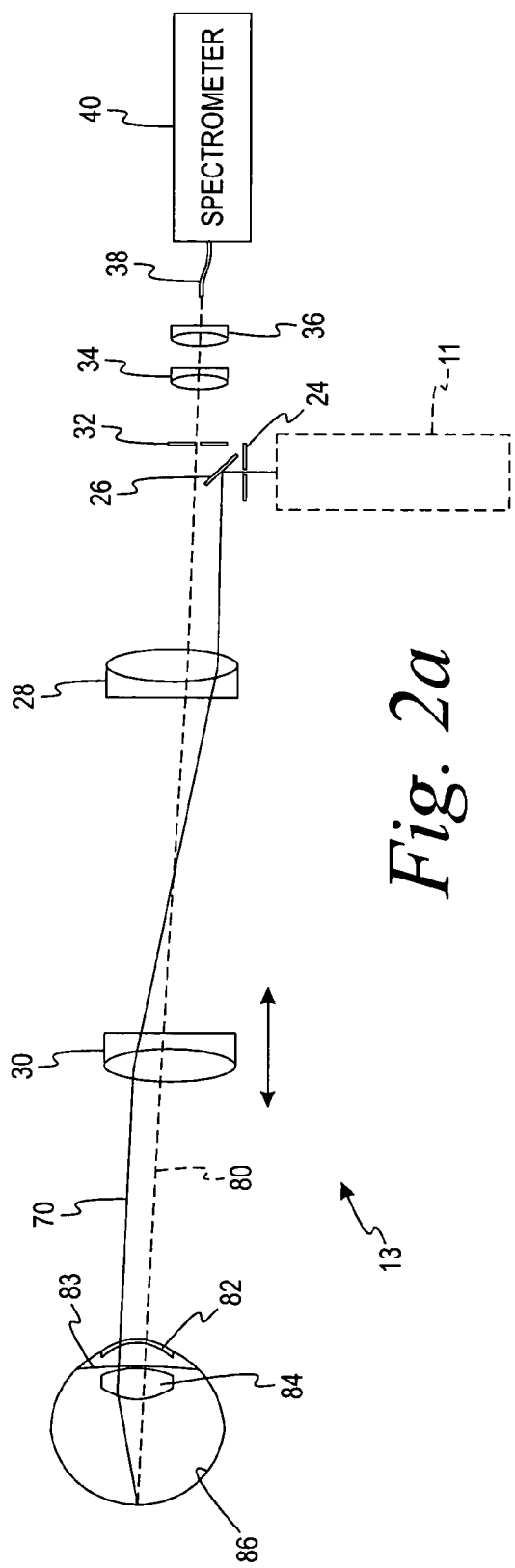
FIG. 2a illustrates the beam separation system of the reflectometry instrument of FIG. 1.

The beam separation system 13 includes an illumination pupil mask 24, a mirror 26, a first lens 28, a second lens 30, a detection pupil mask 32, a third lens 34, and a fourth lens 36. The beam separation system 13 is used for providing an illumination beam to the patient's eye and receiving a detection beam (which has an energy level orders of magnitude less than the illumination beam) that is returned from the patient's macula. As discussed in more detail below, the beam separation system 13 helps to keep the illumination beam and the detection beam separate and distinct by limiting the various "ghost images" and/or reflections that can be present from the inherent reflectance of the illumination beam as it passes through the various components adjacent to the detection beam (e.g., the first and second lenses 28 and 30). If the illumination beam and the detection beam are not kept separate and distinct, then the illumination beam can affect the characteristics of the detection beam before it is received by a fiber 38 that transmits the detection beam to a spectrometer 40 for processing. The details of the paths of the illumination beam and the detection beam within the beam separation system 13 are shown in FIG. 2a.

The light source 12 is provided at a first end 14 of the reflectometry instrument 10. The light source 12 is adapted to emit a beam of white light toward the beam separation system 13. In one embodiment, the light source 12 is a 30 Watt (12 Volt) lamp from Osram, Wotan 642760. However, other white light sources may also be used such as white-light LEDs. The beam of white light emitted from the light source 12 is altered by the components in the source system 11, as discussed below. The beam, which eventually enters the human eye, is referred to herein as the "illumination beam."

After being emitted from the light source 12, the light enters a first source lens system, which includes the source lens 16a and the source lens 16b. The source lenses 16a and 16b form a relay system which images the filament of the light source 12 to the filament mask 20. One type of lens that may be used is the Melles Griot type 01 LAO 014 achromatic lens manufactured by the Optics Group of Melles Griot Corp. of Rochester, N.Y. The detailed specifications of this lens are as follows: Paraxial Focal Length—21.0±0.4 mm; Surface Accuracy—0.5 wave at 546.1 nm; Design Wavelength—488.0 nm, 546.1 nm, 643.8 nm; $f_b$—16.6 mm; $f_f$—20.3 mm; F-Number—1.5; A—22.0 mm; $A_1H$—0.7 mm; $A_2H$— −4.4 mm; B—17.0 mm; Diameter—14+0/−0.15 mm; Clear Aperture—12.6 mm; Center Thickness ($t_c$)—8.1+025 mm; Edge Thickness ($t_e$) 5.8 mm; Material—Crown and flint glasses; Surface Quality—60-40 scratch and dig; Cement—Ultraviolet-cured polyester; Centration—3 arc minutes; Edges 0.25-0.5 mm bevel; Coating—Single Layer $MgF_2$. The source lenses 16a and 16b are short focal achromatic lenses with large diameters versus focal length (high speed). These "high-speed" lenses are especially useful if it is desired to have the target of the illumination beam located at peripheral retinal sites and light for a separate fixation target is passing through more eccentric parts of the lenses 16 of the source system 11.

Between the source lenses 16a and 16b, the illumination beam encounters a pair of filters 18a, 18b. The filter 18a is adapted to cut off light energy in the ultra-violet (UV) range while the filter 18b is adapted to cut off light energy in infrared range. One type of UV filter adequate for use as the filter 18a is a 25 mm round Schott GG395 filter of 3 mm thickness. An example of the filter 18b suitable for use as an infrared filter is a 25 mm round Schott KG2 filter of 3 mm thickness. It should be noted that an infrared filter may not be needed since the level of infrared light leaving the halogen lamp is typically not harmful to the eye and will not affect the measurement of the light-absorbing constituents in the eye (see FIG. 5). Calculations showed that using the ACGIH norms, the safely allowed viewing time was more than 20 minutes for patients with no eye lens, and more then 26 minutes for patients having their natural lens.

Continuing in the direction of the beam separation system 13 of the reflectometry instrument 10, the filament mask 20 includes an opening (e.g., a 2 mm×1 mm opening) through which the illumination beam may travel. Here, unwanted reflections of the glass envelope of the light source 12, and other unwanted stray light sources, are cut off to leave a clean, well-defined illumination beam profile.

After the filament mask 20, there is a second source lens relay system including the source lens 16c and the source lens 16d. The second source lenses 16c and 16d are similar to the first source lenses 16a and 16b, but other lenses may be used as well. The retinal stop 22 is located between the source lenses 16c and 16d in the direction of the beam separation system 13. The retinal stop 22 is used for forming an illumination beam such that the retinal stop 22 defines a circular illumination field of 1 degree at the retina (i.e., about a 300 um diameter). This illumination spot created by the retinal stop 22 is also the visual reference to which the patient fixates. Peripheral measurements are possible if one or more extra holes are drilled in the retinal stop 22 for eccentric fixation. Optional filtering of light through these holes may prevent influence on the detection beam to the spectrometer 40.

In summary, the source system 11 helps to establish some of the characteristics of the illumination beam necessary for measuring the macular pigment of a patient's eye. As illustrated, the source system 11 is shown as being perpendicular to the direction of the illumination beam as the illumination beam enters the patient's eye. However, the source system 11 may be at other angles as well. In such systems, the mirror 26 would be required to be at different angles to redirect the beam into the patient's eye.

Figure 2B:
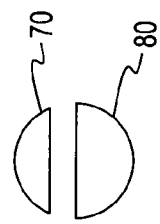
FIG. 2b illustrates the shape of an illumination beam in the patient's pupil after it has passed through an illumination-pupil mask and the spatial portion of the detection beam reflected from the retina as the detection beam passes through the patient's pupil, as dictated by a detection-pupil mask.

Referring now to FIG. 2a, the first component the illumination beam (i.e., represented by the solid line 70) encounters in the beam separation system 13 after passing through the source lens 16d and exiting the source system 11 is the illumination pupil mask 24. The illumination pupil mask 24 has a generally semi-circular shape and determines the shape of the illumination beam as it enters the pupil of the patient's eye. The general profile of the illumination beam 70 as it enters the eye is illustrated in FIG. 2b. Once put into this semi-circular shape, the illumination beam 70 is redirected by the mirror 26. Based on the location of the source system 11 of the illustrated embodiment, the angle for the mirror 26 is about 45° so as to direct the illumination beam 70 toward the first lens 28, the second lens 30 and the patient's eye.

The first lens 28 and the second lens 30 form a Badal system, which helps to keep the magnification constant in the plane of the pupil, while enabling the instrument 10 to be used on eyes with different spherical refraction by moving the second lens 30. The second lens 30 may be moved toward and/or away from the lens 28 via an adjuster 42 (illustrated in FIG. 3). The adjuster 42 is rotated in one direction to move the second lens 30 closer to the lens 28 and rotated in the opposite direction to move the second lens 30 away from the lens 28. However, other methods may be employed to move the second lens 30. The patient may be asked to adjust the second lens via the adjuster 42 until the light appears to be a sharp image. Alternatively, the spectral reflectance detected by the spectrometer 40 may be used to automatically adjust the second lens 30 to the point where the output from the detection beam is at a maximum. A further alternative is to turn the adjuster and set the position at the patient's spectacle prescription, using a scale 44 on top of the instrument 10 as shown in FIG. 3.

To achieve a clean output from the eye for the detection beam (i.e., represented by the dashed line 80), unwanted reflections and ghost images within the beam separation system 13 must be very low, especially in the region of 400-450 nm. "Ghost images" are created on optical systems due to the reflections at surfaces, such as the surfaces created by the first lens 28 and the second lens 30. Light reflected from the (inner) surfaces of lenses may be reflected again to form reasonably well-defined images. These spurious images are often called "ghost images." In prior art reflectometry systems, the reflections and ghost images were not as big of a problem because a dilated pupil was required, yielding a stronger output signal of the detection beam. In the present invention, three independent features in the beam separation system 13 are used to minimize the unwanted reflections and ghost images along the illumination beam 70 flow path, preventing them from entering the detection beam 80 flow path. The first feature relates to a unique anti-reflective coating in the 400 to 450 nm range placed on the first lens 28 and the second lens 30. The second feature relates to the use of two distinct paths (i.e., avoidance of overlap) for the illumination beam 70 and the detection beam 80 through the first lens 28 and the second lens 30, and finally in the frontal parts of the patient's eye. The third feature relates to the beam paths for the illumination beam 70 and the detection beam 80 being offset from the central axis of the first lens 28 and the second lens 30.

As mentioned above and shown in FIG. 2a, the solid line 70 represents the path of the illumination beam while the dashed line 80 represents the path of the detection beam. The first lens 28 and the second lens 30 may have the same specifications as the source lenses 16. However, the coating used on the first lens 28 and the second lens 30 should be one that provides a low reflection, especially in the 400-500 nm range at which the macular pigments affect the detection beam as shown below in FIG. 5 and the reflection from the patient's eye is further reduced to very low levels by the absorption in the eye lens. For example, one type of coating suitable for use with the first lens 28 and the second lens 30 is the Melles Griot' HEBBAR™/074 coating (REBBAR is an acronym for High-Efficiency BroadBand AntiReflection). This advanced multi-layer antireflection coating is optimized to reduce overall reflectance to an extremely low level over the desired spectral range. In particular, the HEBBAR™/074 coating has a maximum reflectance of 1 percent from about 400 nm to about 500 nm, and more specifically less than about 0.3 percent from about 400 nm to about 450 nm for normal incidence.

While the manufacturer only specifies this coating for silica glass, the inventors have surprisingly determined that the HEBBAR™/074 coating also does a fine job in the present invention with a Melles Griot' 01 LAO 014 lens, which is not made of include silica glass. Rather, the Melles Griot' 01 LAO 014 lens is made of crown and flint glasses.

After being redirected by the mirror 26, the illumination beam 70 passes through the first lens 28 and the second lens 30 at locations that are offset from their central axes. Preferably, the illumination beam 70 passes through the first lens 28 and the second lens 30 at a distance of about 3.2 to about 4.7 mm from the center of the lenses 28 and 30. In particular, with the 14.00 mm diameter lenses 28 and 30 that are used, an offset of about 3 mm from the center of the second lens 30 and the central axes of the eye was found to be effective. By not going through the center of the lenses 28, 30, the slight skewness of the beams as they enter the lenses 28 and 30 minimizes specular reflections in the detection beam, such that they are at very low values.

Once through the second lens 30, the illumination beam 70 is suited to enter the eye through the pupil. The illumination beam 70 first passes through a cornea 82 and a lens 84 in the eye. The pupil 83, which does not need to be dilated to use the present invention, controls the amount of ambient light that enters the patient's eye. The illumination beam 70 continues toward a retina 86 in the eye. Upon reaching the retina 86 (and macula), a portion of the illumination beam 70 is reflected from the macula towards the lens 84 and the cornea 82 to form the detection beam 80. As can be seen in FIGS. 2a and 2b, the illumination beam 70 and the detection beam 80 are separated in the frontal parts of the eye (i.e., the cornea 82 and the lens 84). The separation is typically about 0.7 mm in the frontal parts of the eye. Once through the frontal parts of the eye, the detection beam 80 then proceeds back toward the second lens 30.

As illustrated in FIG. 2a, the detection beam 80 remains separated from the illumination beam 70 as the detection beam 80 travels through the lenses 28, 30 toward the spectrometer 40. The detection beam 80 passes through the first lens 28 and the second lens 30 at a distance of about 1.4 mm to about 2.8 mm from the centers of the lenses 28, 30. While the separation is about 0.7 mm in the frontal parts of the eye, the separation in the lenses 28, is only about 0.3 mm. This separation is only possible in combination with small retinal fields (e.g., 1 degree as used herein). If the light paths (both for the illumination and detection beams) from this small retinal field are drawn from the retina through the eye optics and through the first and second lenses 28, 30, they are always separated in the optics with this design, keeping first-order backscatter reflection from these layers from the illumination beam into the detection beam zero.

The detection beam 80 travels through the second lens 30 and the first lens 28 at a position offset from the center. The detection beam 80 does not contact the mirror 26, but instead travels around the mirror 26 as the mirror 26 is not in the path of the detection beam 80. Once past the mirror 26, the detection beam 80 travels through a detection-pupil mask 32. The detection pupil mask 32 is generally semi-circular shaped and determines the shape of the detection beam 80 in the patient's pupil that finally enters the fiber 38. The general profile of the detection beam 80 in the patient's pupil is illustrated in FIG. 2b.

The detection beam 80 then travels through another pair of lenses, the third lens 34 and the fourth lens 36. The third lens 34 and the fourth lens 36 help focus the retinal image of the detection beam 80 for transmission to the fiber 38, which passes the detection beam 80 to the spectrometer 40. Because the third lens 34 and the fourth lens 36 only provide transmission of the detection beam 80, their characteristics are selected for the purpose of achieving a small and sharp image of the 1 degree retinal spot at the fiber tip. One example of a suitable lens for use as the third lens 34 and the fourth lens 36 is the Melles Griot type 01 LAO 001 lens. The detailed specifications of this lens are as follows: Paraxial Focal Length—10.0±0.2 mm; Surface Accuracy—0.5 wave at 546.1 nm; Design Wavelength—488.0 nm, 546.1 nm, 643.8 nm; $f_b$—7.6 mm; $f_f$—9.6 mm; F-Number—1.67; A—10.0 mm; $A_1H$—0.4 mm; $A_2H$— -2.4 mm; B—8.0 mm; Diameter—6.0+0/−0.15 mm; Clear Aperture—5.4 mm; Center Thickness ($t_c$)—4.4±0.25 mm; Edge Thickness ($t_e$)—3.5 mm; Material—crown and flint glasses; Surface Quality—60-40 scratch and dig; Cement—Ultraviolet-cured polyester; Centration—3 arc minutes; Edges 0.25-0.5 mm bevel; Coating—Single Layer $MgF_2$.

The detection beam 80 is brought to a retinal image at the tip of the fiber 38 by the third lens 34 and the fourth lens 36.

The input of the fiber is in the retinal plane, and the size of the fiber determines the detection field at the retina of 1 degree. The fiber 38 has a diameter of 100 um and the magnification of the third lens 34 and the fourth lens 36 is chosen so that it corresponds to 1 degree on the retina.

The spectrometer 40 measures the energy of the detection beam 80 over a specific portion of the electromagnetic spectrum. More specifically, the spectrometer 40 measures the energy of the detected light at wavelength intervals that provide information about the characteristics of the eye. In one embodiment, the spectrometer 40 measures ninety-six wavelengths from 400 nm to 880 nm in 5 nm intervals, which is indicative of the amount of certain constituents (e.g., macular pigment, lens pigmentation, etc.) in the patient's eyes as described in more detail below.

Referring now to FIG. 3, one physical embodiment of the reflectometry instrument 10 is illustrated. The optical components located in the source system 11, as was schematically illustrated in FIG. 1, are located in the portion of the reflectometry instrument 10 enclosed by the dashed line 11. The beam separation system 13, as was schematically illustrated in FIG. 1, and more specifically in FIG. 2, is located in the portion of the reflectometry instrument 10 enclosed by the dashed line 13. As illustrated, the fiber 38 is used to transmit the energy to the spectrometer 40. A patient is positioned at the end of the beam separation system 13, opposite the spectrometer 40. As mentioned above, the reflectometry instrument 10 includes the manual adjuster 42 for moving the second lens 30 (in the beam separation system 13) toward and/or away from the first lens 28 for focusing on the retina of the patient.

The instrument 10 may also include a scale 44 (e.g., measured in diopters) at the top of the instrument 10 that corresponds to movement of the second lens 30. Thus, the adjuster 42 can be manipulated to move the second lens 30 to a location that corresponds to the patient's spectacle prescription. The instrument 10 has to be kept aligned to the eye in 3 dimensions. The distance of the cornea 82 (FIG. 2a) to the lens 30 is optimal at about 20 mm. The transversal movements are necessary to set the combined pupil configuration shown in FIG. 2b at the center of the patient's pupil. In this embodiment, the outer circle of the combined pupil configuration is 3 mm in diameter. Only the illumination beam 70 can be observed, however, by the operator by looking directly at the patient's eye. In another embodiment, the operator could be looking indirectly at the patient's eye by use of a camera mounted in or near the instrument 10.

The movements of the instrument 10 in the three dimensions (up/down, left/right, and back/forth) are accomplished with a translator 48 at the base of the instrument 10, which is mounted on a table 47. Rotation of the instrument around a vertical axes through the eye is possible with a joint 49 and can be locked with the locking mechanism 46. The instrument 10 may also include head rests with temple pads 51 and a chin support 50 mounted on the table 47 to provide the patient with a comfortable fit, while fixing the location of the patient's head (and retina) relative to the second lens 30 in the beam separation system 13.

Figure 4:
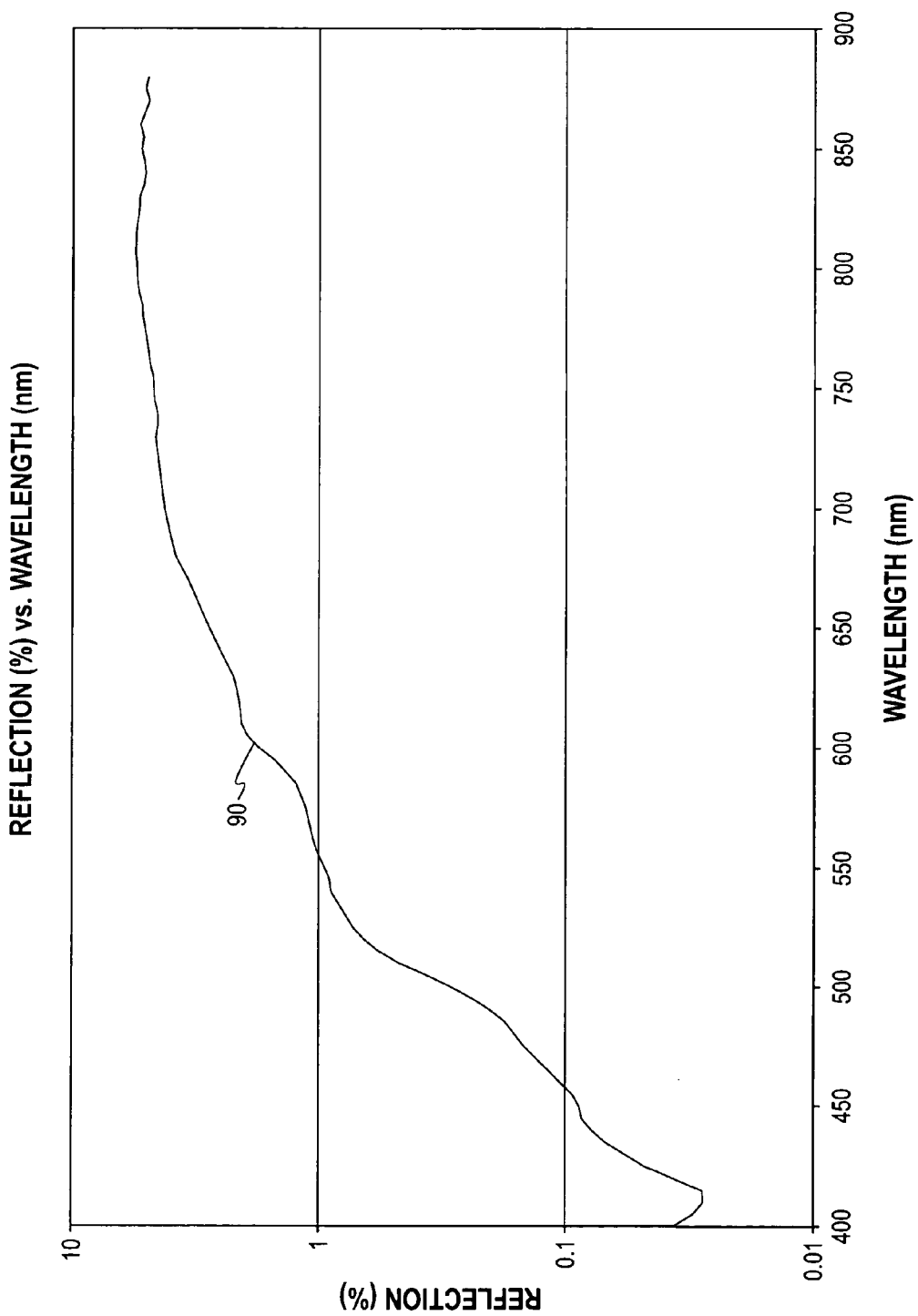
FIG. 4 illustrates the spectral reflectance curve measured by the reflectometry instrument for a first patient.

FIG. 4 illustrates a graph of an actual spectral reflectance curve 90 for a patient as measured by the reflectometry instrument 10 without dilating the patient's pupil. The patient is a male of 55 years of age and is a citizen of The Netherlands. The patient is a non-smoker with fair skin and blue eyes. The patient has what would be considered a normal diet and does not take any nutritional supplements (e.g., lutein supplements or zeaxanthin supplements) that would typically increase the levels of macular pigment.

Figure 7:
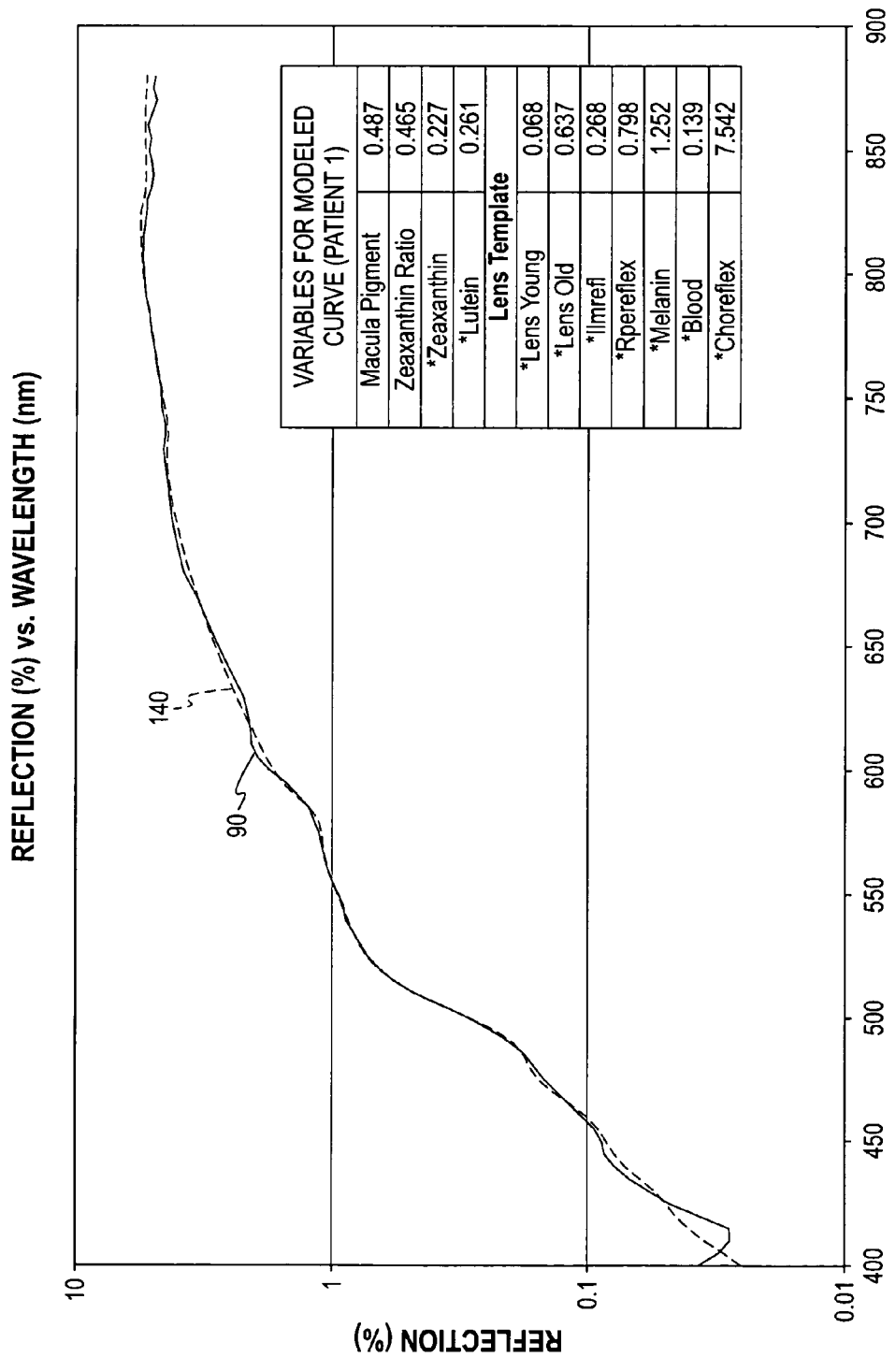
FIG. 7 illustrates the actual spectral reflectance curve for the patient of FIG. 4 as well as a modeled spectral reflectance curve that approximates the actual spectral reflectance curve.
Figure 8:
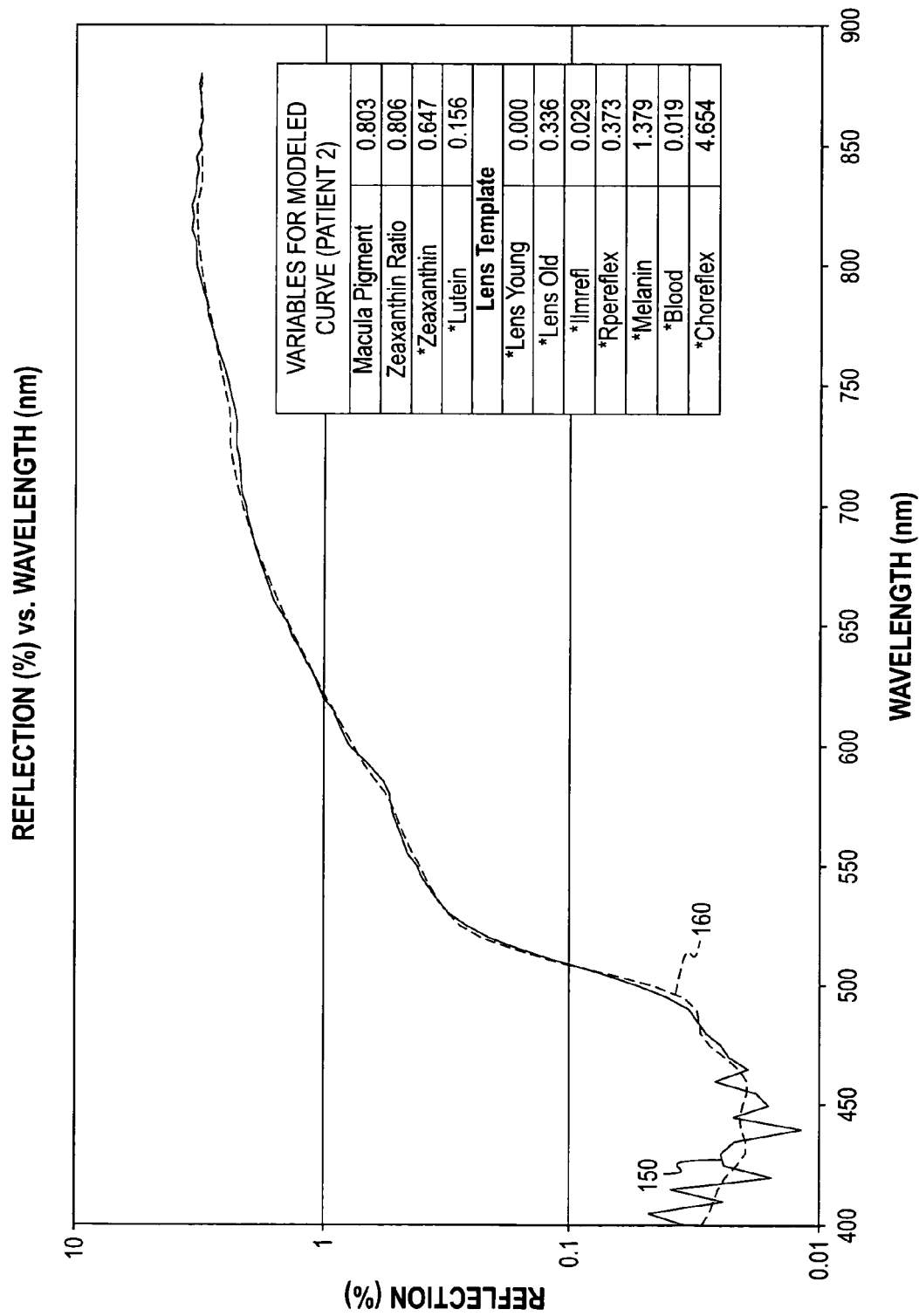
FIG. 8 illustrates the actual spectral reflectance curve for a second patient taking zeaxanthin supplements and the modeled spectral reflectance curve that approximates the second patient's actual spectral reflectance curve.

In the graph of FIG. 4, the X-axis shows the wavelength of light measured in the detection beam that is received by the spectrometer 40. The Y-axis shows the amount of energy for a particular wavelength received from the patient's macula and reflected from the illumination beam. The energy is calibrated against an artificial eye having a retina which has a spectrally neutral (white) reflection of 1%. Therefore, the reflection values in FIGS. 4, 7, and 8 are values that were calibrated against the artificial eye. As an example, for this first patient, about 1% of the energy (or photons) having a wavelength of about 560 nm was reflected from the patient's macula. As can be seen by the curve 90 of FIG. 4, as the wavelength increases to the range of about 800 nm to 900 nm, the amount of reflection that is measured by the spectrometer 40 increases to about 5% for the first patient. As the wavelength decreases towards 400 nm, the amount of reflection drops to very low values, mainly due to absorption in the macular pigment and the lens.

A very large amount of light reflected from the retina never leaves the patient's pupil (i.e. it is reflected internally within the eye). A further reduction in the amount of reflected light occurs due to the mask 32 that cuts off a portion of the detection beam and so forms the small semi-circular detection pupil (see FIG. 2b) of the reflectometry instrument 10. The attenuation due to the size of the semi-circular detection pupil is about 1 to 1000. So, together with the reflection of the macula of 1% at 560 nm, the energy level of the detection beam is roughly 100,000 times smaller than the energy level of the illumination beam. At shorter wavelengths, this ratio is even larger. Hence, even very slight reflections and ghost images caused by the illumination beam can have a significant impact on the detection beam. In an instrument designed for dilated pupils (6 to 8 mm in diameter), the detection pupil can be much larger. This results in a much larger signal in the detection beam, and the impact of ghost image is much more relaxed. The above-mentioned features in the beam separation system 13 that reduce reflections and ghost images help to provide a detection beam containing useful information derived from undilated pupils (i.e., a pupil 2 to 4 mm in diameter).

When the illumination beam is transmitted into the human eye, there are various layers where the light is reflected and various layers where light is absorbed. The relative large reflections from the cornea and lens are not detected by the instrument 10, because of the separation of illumination and detection beams. As such, for modeling purposes, there are three reflectors that must be considered. First, reflection takes place at the internal limiting membrane (ILM), which is adjacent to the vitreous-retina interface. Second, reflection also takes place at the cones and at the retinal pigment epithelium (RPE), which is a layer of melanin located just posterior to the retina and is attached to the choroid. Because it is difficult to discriminate the cone reflection from the RPE reflection, those two reflectors are grouped together. And third, reflection takes place in the choroidal tissue at the back of the eye. The choroid lies between the retina and sclera and is containing layers of blood vessels that nourish the back of the eye and melanin. The reflectance of these layers is assumed to be spectrally neutral.

Figure 5A:
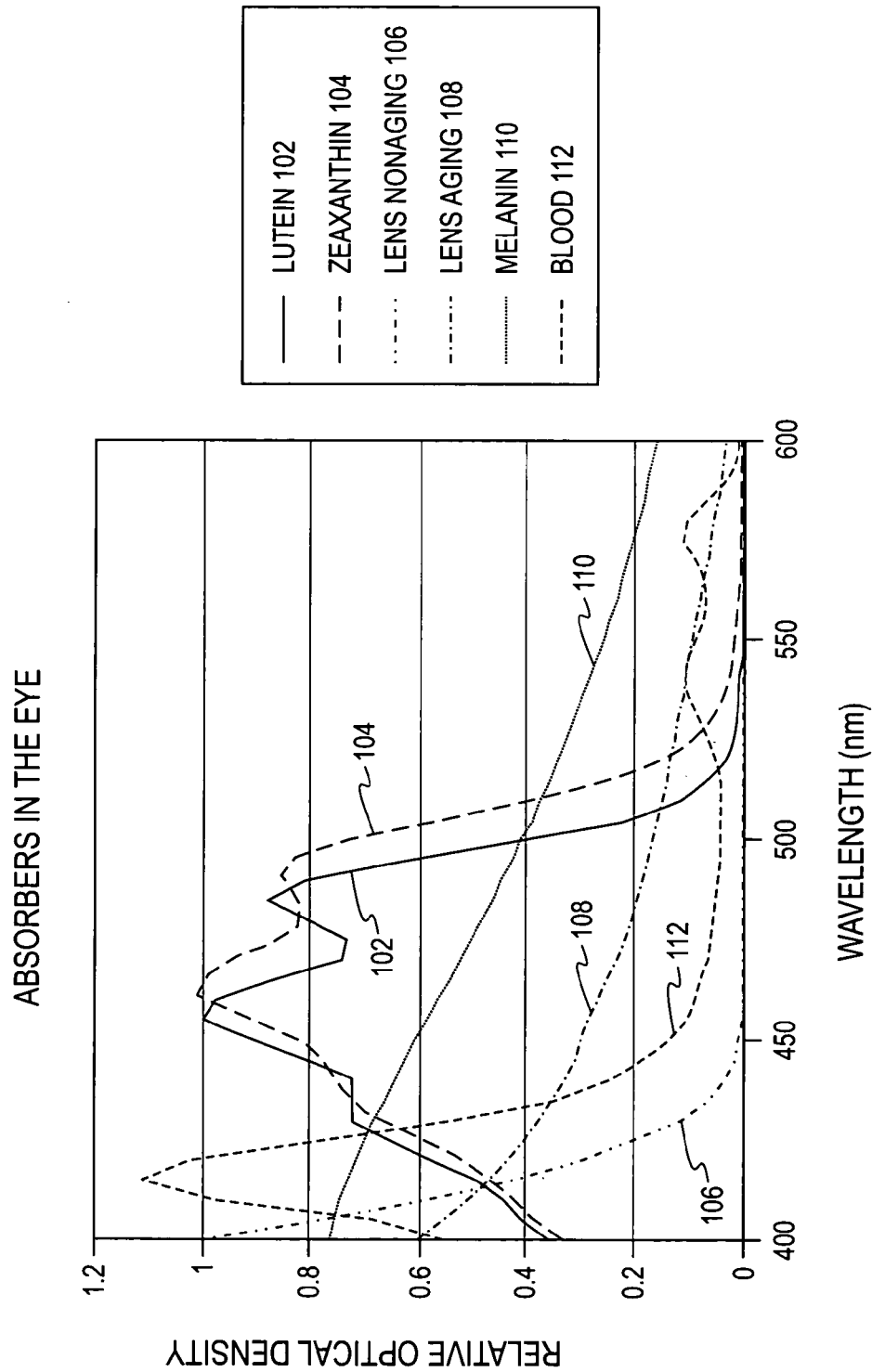
FIG. 5a is a plot of the optical density of various absorbers found in the eye as a function of wavelength.
Figure 5B:
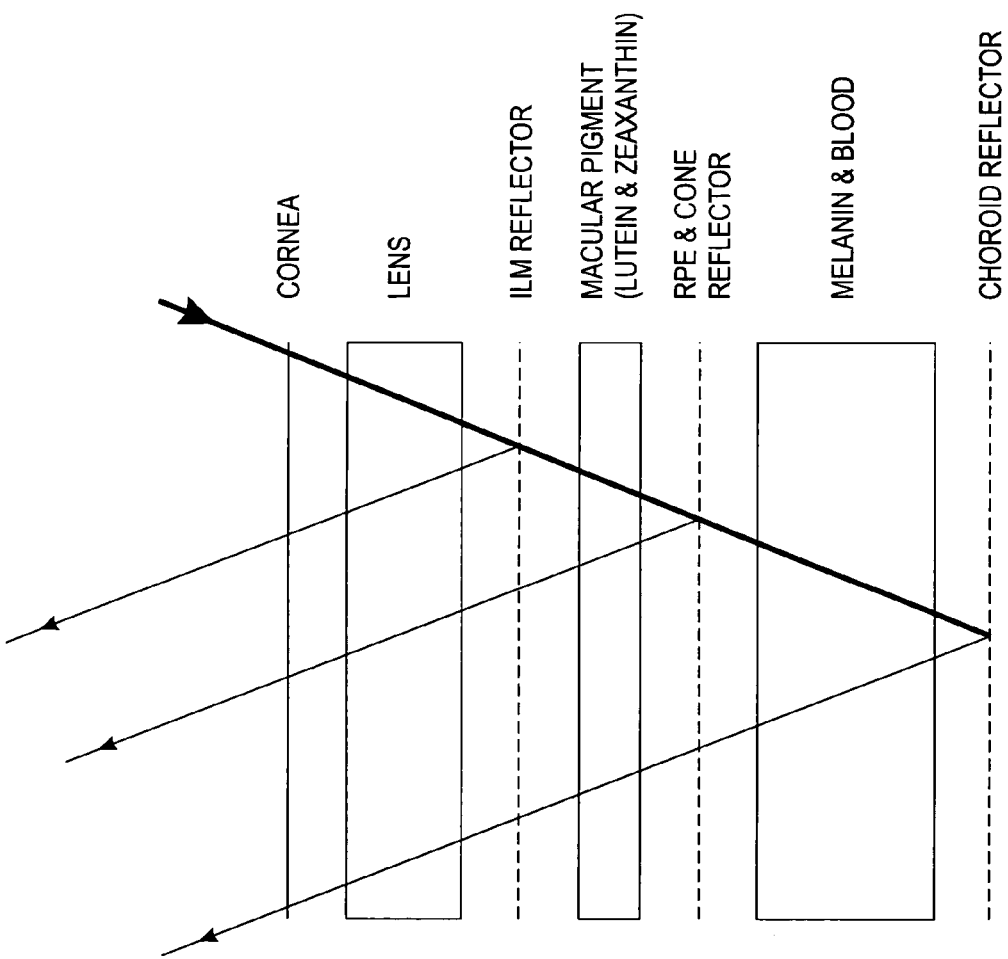
FIG. 5b is schematic showing the various absorbers and various reflectors found in the eye.

FIG. 5a illustrates information about absorbing constituents of the eye that are useful for modeling the optical reflection from the patient's eye. FIG. 5b illustrates the relative positions of the absorbing constituents and the reflective layers in the eye described above. As seen in FIG. 5b, the absorbing layers are positioned between the reflective layers and include pigments in the eye lens, macular pigment, blood, and melanin as shown in FIG. 5a.

The absorbing lens is located between the cornea and the LM. A lens curve 106 of FIG. 5*a* illustrates the absorption of light for a non-aging lens (i.e., the part of the human lens absorption staying constant from a young to an old age). A lens curve 108 of FIG. 5*a* illustrates the absorption of light for an aging lens (i.e., the part of the human lens absorption which increases at older ages). Accordingly, it can be seen that a lens of an older person absorbs light across a broader spectrum. The non-aging lens curve 106 and the aging lens curve 108 were determined in accordance with "Aging of the human lens," Appl. Opt. 26, 1437-1440 (1987). by J. Pokorny, V. C. Smith, and M. Lutze, which is hereby incorporated by reference in its entirety. As such, for the lens of any particular person, the absorption of light can typically be defined by a combination of the lens curve 106 and a certain amount of the lens curve 108. Added to the lens absorption is the fixed amount of absorption from 24 mm of water, mainly from the vitreous and aqueous humor.

The layer with macular pigment, consisting of lutein and zeaxanthin, is positioned between the ILM reflector and the RPE/cone reflector as shown in FIG. 5*b*. A lutein curve 102 of FIG. 5*a* illustrates how lutein in the macula will absorb light. A zeaxanthin curve 104 of FIG. 5*a* illustrates how zeaxanthin in the macula will absorb light. The lutein curve 102 and the zeaxanthin curve 104 were derived by measuring the optical density of lutein and zeaxanthin in olive oil as set forth in "Biological control of primate macular pigment. Biochemical and densitometric studies," Invest. Opthalmol. Vis. Sci. 32, 257-267 (1991) by G. J. Handelman, D. M. Snodderly, N. I. Krinsky, M. D. Russett, and A. J. Adler, which is incorporated by reference in its entirety.

A melanin curve 110 of FIG. 5*a* illustrates the absorption of light for melanin in the eye. The melanin curve 110 was determined in accordance with "Visible and near infrared light absorption in pigment epithelium and choroid," in *Excerpta Medica, International Congress Series*, by V. P. Gabel, R. Birngruber, and F. Hillenkamp, (K. Shimizu and J. A. Oosterhuis, eds., Elsevier, Amsterdam, 1978 pp. 658-662), which is hereby incorporated by reference in its entirety. A blood curve 112 of FIG. 5*a* illustrates the absorption of light for blood in the eye. The blood layer is assumed to be 95% oxygenated and about 20 microns in thickness. The blood curve 112 was determined in accordance with *Spectroscopy of hemoglobin derivatives*, by O. W. van Assendelft, C. C. Thomas, ed., (C. C. Thomas, Springfield, Ill., 1970).

Regarding models of the eye, it should be noted that spectral models for the optical reflection of the human eye have been developed in the past and are detailed in articles such as "Spectral reflectance of the human eye," Vision Res. 26, 313-320 (1986) by D. Van Norren and L. F. Tiemeijer; "Spectral reflectance of the human ocular fundus," Appl. Opt. 28, 1061-1077 (1989) by F. C. Delori and K. P. Pflibsen; and "The pathways of light measured in fundus reflectometry," Vision Res. 36, 2229-2247 (1996) by J. van de Kraats, T. T. J. M. Berendschot, and D. van Norren. These articles are incorporated by reference in their entirety. Such models typically contain various parameters that can be varied, including one or more layers in the retina where reflection takes place as described above (i.e., ILM, cones and RPE, and at the choroid) and layers with absorbing substances (i.e., pigments in the eye lens, macular pigment, blood, and melanin as shown in FIG. 5). By varying several parameters in the model in an automated search scheme, the chi-square difference in spectral reflection from the model and the actual measured spectral reflection from the retina can be minimized and the parameters found by the search scheme are assumed to be in good correspondence with the true values found in the eye.

In prior art modeling systems, however, the macular pigments of lutein and zeaxanthin were grouped together to form a single absorption spectrum and, thus, a single corresponding parameter was used. But, in the present invention, the slightly different absorption curves for both zeaxanthin and lutein are used. While the lutein curve 102 and the zeaxanthin curve 104 are very similar, the slopes near 510 nm are clearly shifted, and the model focuses on closely matching the curves near this wavelength, where the distinction in the absorption of zeaxanthin and lutein is most pronounced. At a wavelength of about 510 nm, the absorption from the other absorbers (i.e., lens, melanin, and blood) in the eye are relatively spectrally neutral (or flat). Therefore, the distinctive spectral fingerprints of zeaxanthin and lutein are useful for deriving unique parameters for both of them.

As set forth above, because zeaxanthin is believed to provide significant advantages over lutein in terms of inhibiting the effects of retinal degeneration, the present invention is useful in determining patients who are in need of zeaxanthin supplementation. For example, the present invention includes the method of determining whether a patient has low levels of zeaxanthin in the macula pursuant to the instrument 10 (FIGS. 1-3) and modeling methodologies set forth herein, and recommending (or administering) certain levels of zeaxanthin supplementation to increase the zeaxanthin pigmentation in the macula. By conducting follow-up periodic testing of the patient, the effects of the zeaxanthin supplementation should become noticeable. Zeaxanthin supplementation can be in the form of daily tablets are capsules, such as those supplements sold by ZeaVision LLC of St. Louis, Mo.

Figure 6:
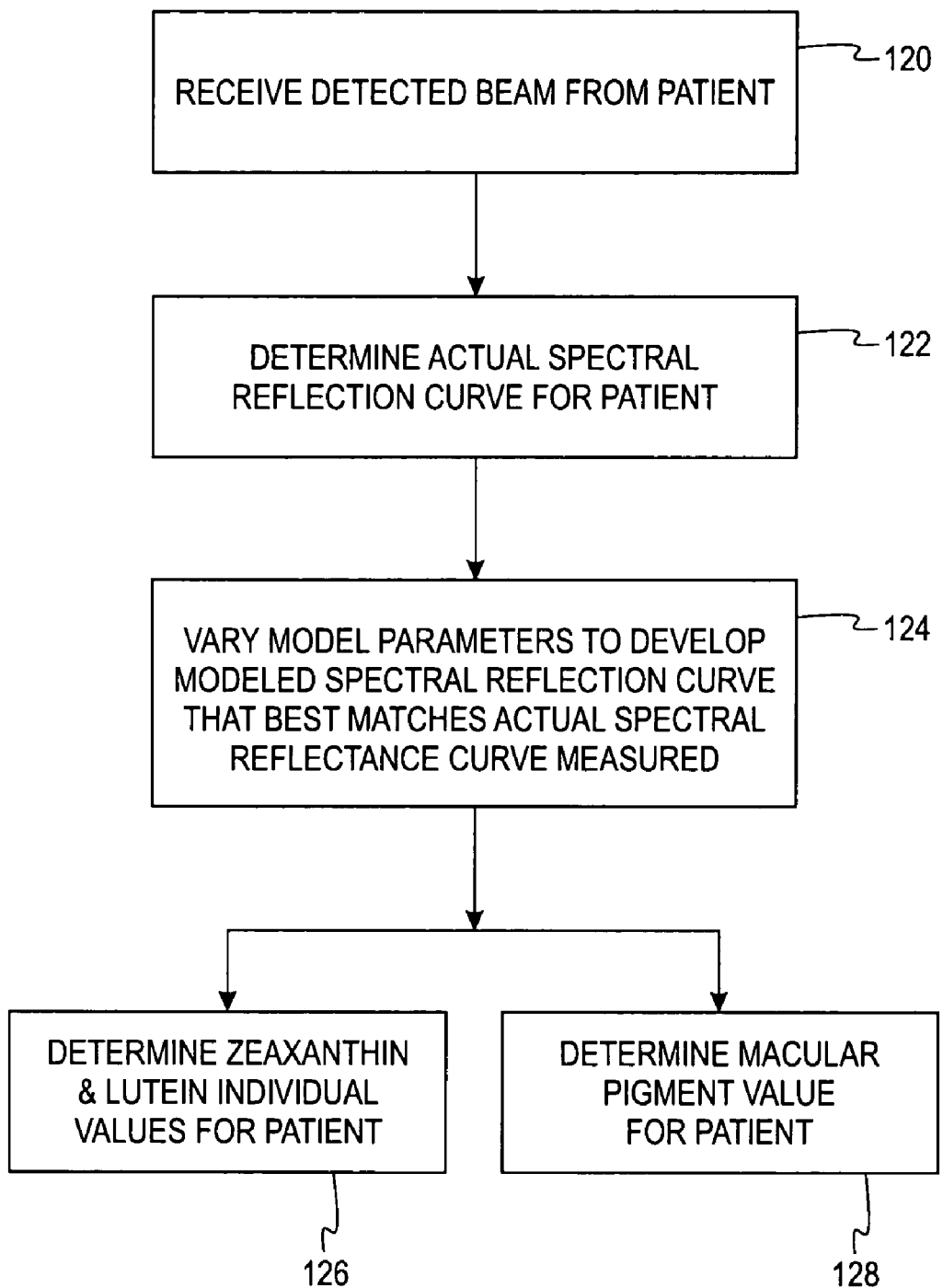
FIG. 6 illustrates a flowchart of the basic acts involved in testing a patient and adjusting parameters in a model to match the patient's spectral reflectance curve as used to determine the patient's macular pigment levels.

FIG. 6 illustrates the general steps that are involved in determining the amounts of macular pigment in a patient, including the use of an eye model to develop a modeled spectral reflectance curve that matches the actual spectral reflectance curve as measured by the spectrometer 40. In particular, at step 120, the patient undergoes a test to produce a detection beam that is reflected from the patient's eye. The instrument 10 of FIGS. 1-3 can be used to perform this function. At step 122, the actual spectral reflectance curve for the patient is determined by calculations involving the calibration spectra from the artificial eye, as mentioned above. At step 124, a model of the human eye varies those parameters discussed above with reference to FIGS. 5*a* and 5*b* to develop a modeled spectral reflection curve that best approximates the actual spectral reflectance curve, such as the actual spectral reflectance curve set forth in FIG. 4 for the first patient.

Once the parameters are optimized to best approximate the actual spectral reflectance curve, the final values for those parameters that are identified in step 124 should be close to the actual values of those parameters in the patient's eye. As such, the model can be used to output the overall macular pigment value for the patient, as set forth in step 128. Or, the model can be used to output the individual zeaxanthin macular pigment value, the individual lutein macular pigment value, the overall macular pigment value, and the individual zeaxanthin fraction for the patient, as set forth in step 126.

Typically, this value for the macular pigment is referred to as the patient's macular pigment optical density ("MPOD"), which is a dimensionless number indicative of the amount of pigment located at the macula. It should be noted that the MPOD as measured by one form of instrument, such as the reflectometry instrument 10, may be different from the MPOD measured by another form of instrument, such as a heterochromatic flicker photometry instrument. Nevertheless, the skilled artisan will recognize that correlations can be developed between the MPOD values of a first type of instrument and the MPOD values of a second type of instrument.

Regarding the actual curve-fitting process of step 124, the model uses the Marquardt-Levenberg (Press et al. 1989) search algorithm to determine the several parameters involved simultaneously. This algorithm is capable of fitting the non-linear parameters in this model with parallel pathways. The Marquardt-Levenberg non-linear procedures are set forth in *Numerical Recipes in C*, and *The Art of Scientific Computing*, Cambridge University Press: Cambridge 1992, to Press et al, which are herein incorporated by reference in their entireties. Weighting of the spectral data points is applied, based on the standard deviation between two succeeding 1 second measurements, but other forms of weighting may be applied.

FIG. 7 illustrates the actual spectral reflectance curve 90 of FIG. 4 along with a modeled spectral reflectance curve 140 for the first patient. The modeled spectral reflectance curve was developed by varying the parameters set forth above with respect to FIG. 5. As can be seen, the modeled spectral reflectance curve 140 approximates the actual spectral reflectance curve 90 over the spectrum of 400 nm to 900 nm, and closely approximates the actual spectral reflectance curve 90 in the range of about 400 nm to about 500 nanometers, the range at which the effects of the macular pigment are most pronounced, as can be seen in FIG. 5.

FIG. 7 also includes the actual values of the various parameters that were used to develop the modeled spectral reflectance curve 140 (i.e. the values from step 124 in FIG. 6). The overall macular pigment optical density (MPOD) was determined by the model to be 0.487, of which 0.227 was attributed to zeaxanthin and 0.261 was attributed to lutein. The zeaxanthin ratio of 0.465 merely represents the ratio of the zeaxanthin value to the total macular pigment value (i.e., 46.5% of the macular pigment was zeaxanthin) The values of the non-aging (young) lens and aging (old) lens parameters was determined to be 0.068 and 0.637, respectively. The other absorbers, melanin and blood, had values of 1.252 and 0.139 mm, respectively.

Regarding the three reflector values, the Choroid reflectance was determined to be 7.542%. The inner limiting membrane (ILM) reflectance was determined to be 0.268%. And, the reflectance of the retinal pigment epithelium (RPE) and cones was determined to be 0.798%.

The instrument 10 and the modeling techniques set forth above were used to measure the eye parameters for twenty different individuals from The Netherlands. The first patient referred to in FIG. 7 was also one of the twenty patients. For each individual, the test was run four times to determine an average value for that individual. The group of twenty individuals ranged in age from 19 to 79 and none of the twenty individuals ingested lutein and zeaxanthin supplements on a daily basis that could affect the pigmentation in the macula. According to this data, the average lutein-MPOD value for the twenty individuals is 0.16 and the average zeaxanthin-MPOD value is 0.39. The average total MPOD value was 0.55 (0.16+0.39) and the average zeaxanthin ratio was 0.68. For the total MPOD value, the standard deviation was 0.21. For the zeaxanthin ratio, the standard deviation was 0.14.

FIG. 8 illustrates the actual spectral reflectance curve 150 and the modeled spectral reflectance curve 160 for a second patient who regularly takes zeaxanthin supplements. The second patient is a male of 53 years of age and is a citizen of the United States. The second patient, who is a non-smoker, has fair skin and blue eyes. The second patient has an average diet, but has taken at least 10 mg of zeaxanthin on a daily basis for nearly three years prior to the tests conducted by the instrument 10. The table below illustrates the nine of the ten sets of test results related to macular pigment measurements for the second patient as determined by the model for the second patient. One set of test results was discarded because it appeared to involve some type of test malfunction as the values were very skewed compared to the other nine results. Test # 1 in the table below reflects the outcome shown with respect to FIG. 8.

| Test # | Macular Pigment | Zeaxanthin Ratio | Zeaxanthin | Lutein |
|--------|-----------------|------------------|------------|--------|
| Test 1 | 0.803 | 0.806 | 0.647 | 0.156 |
| Test 2 | 1.059 | 0.576 | 0.610 | 0.449 |
| Test 3 | 0.868 | 0.716 | 0.621 | 0.247 |
| Test 4 | 0.869 | 0.798 | 0.693 | 0.176 |
| Test 5 | 0.790 | 0.935 | 0.739 | 0.051 |
| Test 6 | 0.839 | 0.773 | 0.648 | 0.191 |
| Test 7 | 0.759 | 0.864 | 0.656 | 0.103 |
| Test 8 | 0.602 | 0.790 | 0.476 | 0.126 |
| Test 9 | 0.835 | 0.680 | 0.568 | 0.267 |
| Average | 0.825 | 0.771 | 0.629 | 0.196 |

As can be seen from this table, the average level of zeaxanthin determined by the model was much higher in the second patient than in the first patient. The average level of zeaxanthin for the second patient was also higher than the average of the 20 test subjects described above. Furthermore, the spectral reflectance curves for the second patient (FIG. 8) between 400 nm and 500 nm was substantially lower than the spectral reflectance curve for the first patient (FIG. 7). Accordingly, the model has predicted that the second patient has higher levels of zeaxanthin in the macula, which should be the case considering the three-year zeaxanthin supplementation by the second patient.

It should be also noted that the techniques described above with respect to macular pigment also apply to the determination of characteristics of the lens within the eye. Accordingly, the present invention may also be useful for determining the early stages of aging of the human lens or first signs of cataract formation, without needing to dilate the patient's eyes.

Each of these embodiments and obvious variations thereof is contemplated as falling within the spirit and scope of the claimed invention, which is set forth in the following claims.

The invention claimed is:

1. A reflectometry instrument to measure macular pigment of a macula of a human eye, comprising:
    a light source for emitting an illumination beam in a direction toward the macula;
    a spectrometer for measuring a detection beam, the detection beam being a portion of the illumination beam reflected from the macula, the detection beam being indicative of the amount of macular pigment in the macula;
    a first lens for transmitting the illumination beam to the macula and for transmitting the detection beam from the macula to the spectrometer, the first lens including an anti-reflection coating; and
    a second lens adjacent to the first lens, the second lens being adapted to transmit the illumination beam to the macula and for transmitting the detection beam from the macula to the spectrometer, the second lens including an anti-reflection coating,
    wherein the illumination beam and the detection beam remain separated when the illumination beam and the detection beam pass through the first lens and the second lens.

2. The reflectometry instrument of claim 1, wherein the anti-reflection coatings of the first lens and the second lens has a maximum reflectance of 1 percent in the range of about 400 nm to about 500 nm for normal light incidence.

3. The reflectometry instrument of claim 2, wherein the anti-reflection coatings have a reflectance less than 0.3 percent in the 400-450 nm range for normal light incidence.

4. The reflectometry instrument of claim 3, wherein the first lens and the second lens are made of material including crown and flint glasses.

5. The reflectometry instrument of claim 1, wherein the illumination beam and the detection beam are transmitted through the first lens and the second lens at locations offset from the centers of the first and second lenses.

6. The reflectometry instrument of claim 1, wherein the separation of the illumination beam and detection beams occurs in the first and second lens and frontal parts of the eye when using a retinal field of about 1 degree.

7. The reflectometry instrument of claim 1, wherein the separation of the illumination beam and detection beams occurs in an undilated pupil of the eye.

8. The reflectometry instrument of claim 1, further comprising a mirror for turning the illumination beam from the light source toward the first lens, the detection beam being adapted to pass by the mirror without contacting the mirror, the spectrometer being located behind the mirror.

9. The reflectometry instrument of claim 1, in combination with computer code that varies and determines eye-related variables to create a modeled spectral reflectance curve that approximates an actual spectral reflectance curve measured by the spectrometer, at least one of the eye-related variables being a macular pigment amount.

10. The reflectometry instrument of claim 1, in combination with computer code that varies and determines eye-related variables to create a modeled spectral reflectance curve that approximates an actual spectral reflectance curve measured by the spectrometer, at least one of the eye-related variables being a lutein-macular pigment amount and at least one of the eye-related variables being a zeaxanthin-macular pigment amount.

11. A reflectometry instrument to measure macular pigment of a macula of a human eye, comprising:
    a light source for emitting an illumination beam in a direction toward the macula;
    a spectrometer for measuring a detection beam, the detection beam being a portion of the illumination beam reflected from the macula, the detection beam being indicative of the amount of macular pigment in the macula;
    a first lens for transmitting the illumination beam to the macula and for transmitting the detection beam from the macula to the spectrometer, the illumination beam and the detection beam being transmitted by the first lens at a location offset from the center of the first lens; and
    a second lens adjacent to the first lens, the second lens for transmitting the illumination beam to the macula and for transmitting the detection beam from the macula to the spectrometer, the illumination beam and the detection beam being transmitted by the second lens at a location offset from the center of the second lens,
    wherein the illumination beam and the detection beam remain separated when the illumination beam and the detection beam pass through the first lens and the second lens.

12. The reflectometry instrument of claim 11, wherein the transmission of the illumination beam and the detection beam through the first lens and the second lens occurs at locations that are offset from the centers of the first lens and the second lens, respectfully, by a distance in the range from about 1 mm to about 4 mm.

13. The reflectometry instrument of claim 12, wherein the offset distance is about 3 mm.

14. The reflectometry instrument of claim 11, wherein the first and second lens include crown and flint glasses and include anti-reflection coatings, the reflectance of the anti-reflection coatings being below 1 percent in the range of about 400 nm to about 500 nm for normal light incidence.

15. The reflectometry instrument of claim 14, wherein the anti-reflection coating includes a reflectance below 0.3 percent in the 400 nm to 450 nm range for normal light incidence.

16. The reflectometry instrument of claim 11, wherein the separation of the illumination beam and detection beams occurs in the first and second lens and the frontal parts of the eye when using a retinal field of about 1 degree.

17. The reflectometry instrument of claim 11, wherein the illumination beam travels along an illumination path, the detection beam travels along a detection path, the illumination path and the detection path intersect between the first and second lenses.

18. The reflectometry instrument of claim 11, in combination with computer code that varies and determines eye-related variables to create a modeled spectral reflectance curve that approximates an actual spectral reflectance curve measured by the spectrometer, at least one of the eye-related variables being a macular pigment amount.

19. The reflectometry instrument of claim 11, in combination with computer code that varies and determines eye-related variables to create a modeled spectral reflectance curve that approximates an actual spectral reflectance curve measured by the spectrometer, at least one of the eye-related variables being a lutein-macular pigment amount and at least one of the eye-related variables being a zeaxanthin-macular pigment amount.

20. A method of determining the amount of macular pigment in the macula of a human eye, comprising:
    passing an illumination beam through a lens system having a first lens and a second lens, the illumination beam passing through the first lens and the second lens at locations offset from the centers of the first lens and second lens;
    directing the illumination beam from the lens system onto the macula so as to produce a detection beam that reflects from the eye; were
    passing the detection beam through the lens system offset from the centers of the first lens and second lens, the detection beam remaining separated from the illumination beam at the first lens and the second lens;
    receiving the detection beam at a spectrometer; and
    measuring characteristics of the detection beam at the spectrometer.

21. The method of claim 20, wherein the illumination beam travels along an illumination path and the detection beam travels along a detection path in the lens system, and wherein the passing the illumination beam includes:
    producing the illumination beam from a source in a direction that is transverse to the illumination path, and
    reflecting the illumination beam with a mirror so as to pass the illumination beam along the illumination path through the lens system.

22. The method of claim 21, wherein the illumination beam passes through an illumination mask prior to the reflecting the illumination beam with the mirror to cause the illumination beam to have a partial-circle beam profile.

23. The method of claim 22, wherein the detection beam passes by the mirror without contacting the mirror, the spectrometer being located behind the mirror.

24. The method of claim 22, wherein the detection beam passes through a detection mask subsequent to the passing by the mirror to cause the detection beam to have a partial-circle beam profile.

25. The method of claim 21, wherein the source includes a halogen lamp and filters for filtering ultraviolet energy from the illumination beam.

26. The method of claim 25, wherein the source further includes lenses and masks for producing a beam size for passing to an undilated pupil.

27. The method of claim 20, wherein the first and second lens include a coating that has a reflection that is less than about 0.3% in the range of about 400 to about 450 nm for normal light incidence.

28. The method of claim 20, further including creating a modeled spectral reflectance curve that approximates an actual spectral reflectance curve measured by the spectrometer, the creating includes determining values for a plurality of eye-related variables.

29. The method of claim 28, wherein one of the plurality of eye-related variables is an amount of macular pigment.

30. The method of claim 28, wherein one of the plurality of eye-related variables is an amount of zeaxanthin macular pigment and another of the plurality of eye-related variables is an amount of lutein macular pigment.

31. The method of claim 28, wherein one of the plurality of eye-related variables relates to a characteristic of the lens in the eye.

32. The method of claim 31, wherein the characteristic is indicative of the patient having a cataract.

33. A reflectometry instrument to measure a lens characteristics of a human eye, comprising:
  a light source for emitting an illumination beam in a direction toward the eye;
  a spectrometer for measuring a detection beam, the detection beam being a portion of the illumination beam reflected from the eye, the detection beam being indicative of the lens characteristic in the eye;
  a first lens for transmitting the illumination beam to the eye and for transmitting the detection beam from the eye to the spectrometer, the first lens including an anti-reflection coating; and
  a second lens adjacent to the first lens, the second lens being adapted to transmit the illumination beam to the eye and for transmitting the detection beam from the eye to the spectrometer, the second lens including an anti-reflection coating,
  wherein the illumination beam and the detection beam remain separated when the illumination beam and the detection beam pass through the first lens and the second lens.

34. The instrument of claim 32, wherein the lens characteristic is indicative of the patient having a cataract.

35. The instrument of claim 32, wherein the anti-reflection coatings of the first lens and the second lens has a maximum reflectance of 1 percent in the range of about 400 nm to about 500 nm.

36. The instrument of claim 32, wherein the illumination beam and the detection beam are transmitted through the first lens and the second lens at locations offset from the centers of the first and second lenses.

* * * * *